(12) United States Patent
DeGreeff et al.

(10) Patent No.: US 10,648,955 B2
(45) Date of Patent: May 12, 2020

(54) ONLINE CHEMICAL DERIVATIZATION USING A COOLED PROGRAMMED TEMPERATURE VAPORIZATION INLET

(71) Applicant: The Government of the United States of America, as represented by the Secretary of the Navy, Arlington, VA (US)

(72) Inventors: Lauryn E. DeGreeff, Washington, DC (US); Christopher J. Katilie, Washington, DC (US)

(73) Assignee: The Government of the United States of America, as represented by the Secretary of the Navy, Washington, DC (US)

( * ) Notice: Subject to any disclaimer, the term of this patent is extended or adjusted under 35 U.S.C. 154(b) by 248 days.

(21) Appl. No.: 15/903,166

(22) Filed: Feb. 23, 2018

(65) Prior Publication Data
US 2018/0246070 A1    Aug. 30, 2018

Related U.S. Application Data

(60) Provisional application No. 62/463,045, filed on Feb. 24, 2017.

(51) Int. Cl.
*G01N 30/12*  (2006.01)
*G01N 30/20*  (2006.01)
*G01N 30/30*  (2006.01)
*G01N 30/06*  (2006.01)
G01N 30/02  (2006.01)
(Continued)

(52) U.S. Cl.
CPC .............. *G01N 30/12* (2013.01); *G01N 30/06* (2013.01); *G01N 30/20* (2013.01); *G01N 30/30* (2013.01);
(Continued)

(58) Field of Classification Search
CPC .............. C07C 69/96; G01N 2030/025; G01N 2030/042; G01N 2030/067;
(Continued)

(56) References Cited

U.S. PATENT DOCUMENTS 5,783,450 A * 7/1998 Yoshida ................. G01N 30/88
422/70
7,534,331 B2 * 5/2009 Kayyem ............... B01L 3/5027
204/403.01
(Continued)

OTHER PUBLICATIONS

Collins et al., "Trace explosives sensor testbed (TESTbed)" Review of Scientific Instruments 88, 034104 (Mar. 30, 2017).
(Continued)

*Primary Examiner* — Francis C Gray
(74) *Attorney, Agent, or Firm* — US Naval Research Laboratory; Joseph Grunkemeyer

(57) ABSTRACT

A method of detecting an analyte by: providing a derivatizing agent that is reactive with the analyte; delivering the derivatizing agent into a chamber; delivering a sample of a gas suspected of containing the analyte into the chamber before or after delivering the derivatizing agent, while the chamber is maintained at a temperature that retains the derivatizing agent and any analyte and that allows reaction between the derivatizing agent and any analyte in the chamber to form a derivatized analyte; warming the chamber to cause evaporation of any derivatized analyte; and delivering the derivatized analyte in the chamber into a gas chromatograph column.

19 Claims, 5 Drawing Sheets

(51) Int. Cl.
*C07C 69/96* (2006.01)
*G01N 30/04* (2006.01)

(52) U.S. Cl.
CPC ........ *C07C 69/96* (2013.01); *G01N 2030/025* (2013.01); *G01N 2030/042* (2013.01); *G01N 2030/067* (2013.01); *G01N 2030/126* (2013.01); *G01N 2030/201* (2013.01)

(58) Field of Classification Search
CPC ....... G01N 2030/126; G01N 2030/201; G01N 30/06; G01N 30/12; G01N 30/20; G01N 30/30
See application file for complete search history.

(56) References Cited

U.S. PATENT DOCUMENTS

| | | | | |
|---|---|---|---|---|
| 2006/0063268 | A1* | 3/2006 | Prest | B01D 1/00 436/86 |
| 2006/0163471 | A1* | 7/2006 | Zapata | G01N 27/624 250/288 |
| 2009/0111189 | A1* | 4/2009 | Schroeder | G01N 30/88 436/81 |
| 2011/0301063 | A1* | 12/2011 | Netzel | G01N 30/72 506/12 |
| 2013/0337477 | A1* | 12/2013 | Kuhr | G01N 1/22 435/7.92 |
| 2014/0011284 | A1* | 1/2014 | Lavold | B01D 15/3852 436/120 |
| 2017/0067894 | A1* | 3/2017 | Helman | G01N 33/5091 |
| 2017/0336341 | A1* | 11/2017 | Kuhr | G01N 1/2214 |
| 2018/0246070 | A1* | 8/2018 | DeGreeff | G01N 30/06 |

OTHER PUBLICATIONS

Lubrano et al., "Analysis of ammonium nitrate headspace by on-fiber solid phasemicroextraction derivatization with gas chromatography massspectrometry" Journal of Chromatography A, 1429 (2016) 8-12.

* cited by examiner

ONLINE CHEMICAL DERIVATIZATION USING A COOLED PROGRAMMED TEMPERATURE VAPORIZATION INLET

This application claims the benefit of U.S. Provisional Application No. 62/463,045, filed on Feb. 24, 2017. The provisional application and all other publications and patent documents referred to throughout this nonprovisional application are incorporated herein by reference.

TECHNICAL FIELD

The present disclosure is generally related to gas chromatography.

DESCRIPTION OF RELATED ART

As many as 80-90% of known organic compounds are not amenable to gas chromatography (GC), mostly due to thermal instability or low volatility. Derivatization is often used to improve the chromatographic suitability of such analytes. In a derivatization reaction, the analyte of interest is mixed with a derivatizing agent resulting in a new species that is more compatible for GC separation and detection. The reaction may occur prior to the injection or directly on the GC column; however, pre-injection derivatization is far more common. Derivatization may result in a new species that has increased volatility if it would otherwise not elute, has decreased volatility if it was too low in mass for good separation or peak shape, has enhanced thermal stability, has improved detector response, or has improved separation or peak shape. Examples of derivatization reactions include silylation, where an active hydrogen is replaced with a trialkylslyl group. This reduces the polarity of the analyte and decreases its tendency to hydrogen bond with the column stationary phase, thus increasing volatility and reducing reactivity. Also, acylation converts alcohols or amines to more stable species, or alkylation replaces a reactive hydrogen with an alkyl group (Robards et al., "Gas Chromatography" in *Principles and Practice of Modern Cromatographic Methods*; Elsevier Ltd., New York (2004) pp. 149-154).

BRIEF SUMMARY

Disclosed herein is a method of detecting an analyte comprising: providing a derivatizing agent that is reactive with the analyte; delivering the derivatizing agent into a chamber; delivering a sample of a gas suspected of containing the analyte into the chamber before or after delivering the derivatizing agent, wherein the chamber is maintained at a temperature that retains the derivatizing agent and any analyte and that allows reaction between the derivatizing agent and any analyte in the chamber to form a derivatized analyte; warming the chamber to cause evaporation of any derivatized analyte; and delivering the evaporated derivatized analyte into a gas chromatograph column.

Also disclosed herein is a method of detecting an analyte comprising: delivering an internal standard into a chamber; delivering a sample of a gas suspected of containing the analyte into the chamber before or after delivering the internal standard, wherein the chamber is maintained at a temperature that retains the internal standard and any analyte; warming the chamber to cause evaporation of the internal standard and any analyte; and delivering the evaporated internal standard and analyte into a gas chromatograph column.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

The method disclosed herein allows for the simultaneous derivatization and trapping of vaporous analytes on a programmed temperature vaporization (PTV) inlet. The PTV inlet is cooled to trap both the derivatizing agent and the analyte of interest. The analyte is derivatized in the cooled inlet and the resulting species is desorbed directly onto the head of a gas chromatography column.

Derivatization is most commonly done by physically mixing the derivatizing agent with the analyte of interest prior to injection into the GC inlet. This creates the new species that now have the necessary attributes for proper retention by a chromatographic stationary phase or for detection by the instrument of choice. This method is not amenable to vaporous analytes. Alternatively, solid phase microextraction (SPME), an extraction technique that is amenable to the collection of vaporous analytes, may be used with derivatization. In such a protocol, the SPME fiber is exposed to the derivatizing agent, followed by the analyte vapor, or vice versa. The derivatization reaction then occurs on the fiber. The new species is thermally desorbed in the traditional inlet of a gas chromatograph. The method described herein simplifies or eliminates several steps in the previous SPME approach. Specifically, utilizing the online derivatization (a) eliminates the need for an internal standard for quantitation, and (b) reduces the amount of consumables required compared to the SPME approach.

Figure 1:
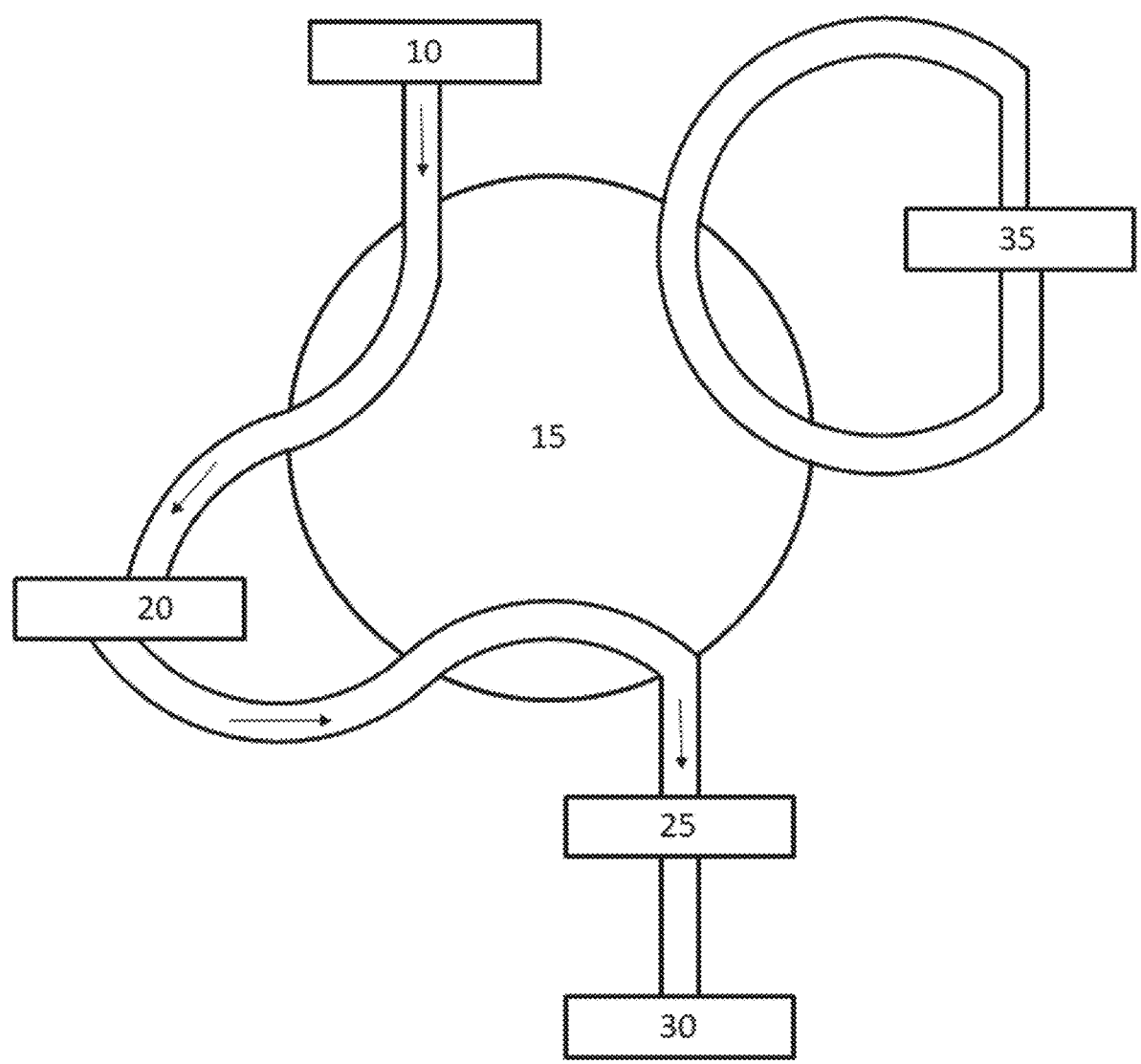
FIG. 1 schematically illustrates delivery of the derivatizing agent to the chamber.

The first step in the method is schematically illustrated in FIG. 1. A carrier gas source 10 delivers the carrier gas into one port of a six-port valve 15. Such six-port valves are commonly used with gas chromatographs, however any system of tubes and valves that delivers the materials according to the present method may be used. The gas then flows through a derivatizing agent source 20 where it picks up derivatizing agent into the gas stream. The derivatizing agent is then delivered back through the six-port valve 15 and into the chamber 25.

Figure 2:
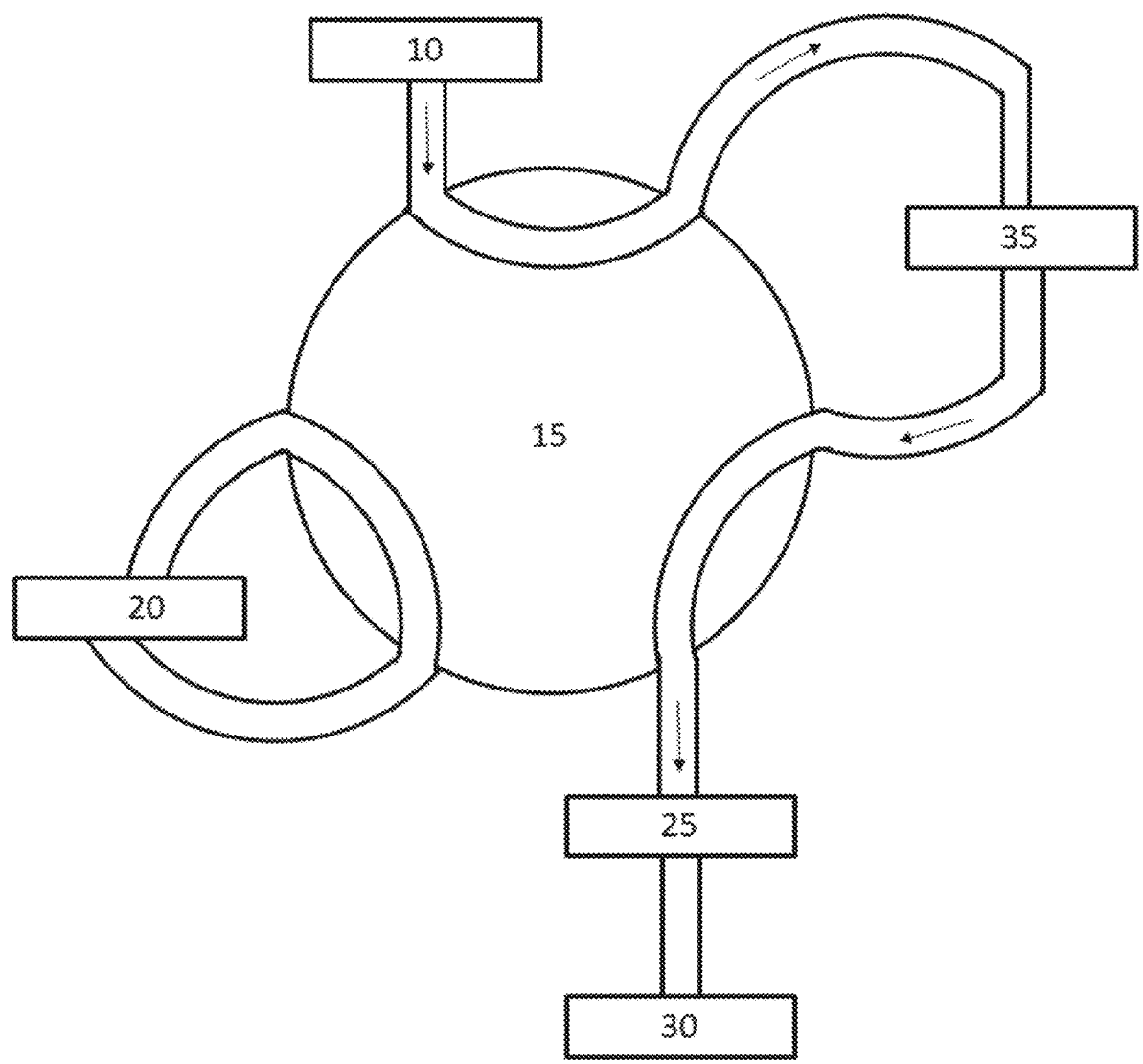
FIG. 2 schematically illustrates delivery of the sample to the chamber.

Next, as schematically illustrated in FIG. 2, the six-port valve 15 is rotated so that the carrier gas passes through a sample source 35 where it picks up a sample that may or may not contain the analyte. Any analyte is then delivered back through the six-port valve 15 and into the chamber 25. The steps of delivering the derivatizing agent and the sample to the chamber 15 may be performed in either order.

The chamber 25 may be a PTV inlet or any other suitable temperature controlled device that can retain the derivatizing agent, analyte, and derivatized analyte. Initially the chamber is maintained at a temperature where the derivatizing agent and analyte are retained in the chamber, but which allows a reaction between these compounds to form a derivatized analyte. This may be below the melting point of the compounds and may be below room temperature. A suitable temperature may be determined empirically by subsequent detection of the derivatized analyte by the gas chromatograph. Other vents, valves, and/or tubes may be present to avoid letting the gas, possibly contaminated with derivatizing agent or analyte from entering the gas chromatograph at this stage. A Gerstel online-CIS switch may be used for this purpose.

In an optional step, an internal standard, generally a compound chemically similar to the analyte of interest (in the case of ammonia derivatizatioin, diethylamine could be used) is also delivered to the chamber 25. This may occur in any sequence with delivering the derivatizing agent and the sample. The internal standard may be vaporous, but would also be retained in the cooled chamber and released upon warming. There would be no reaction with with the analyte. The internal standard may also be used without the derivatizing agent for analytes that can be detected without being derivatized.

Figure 3:
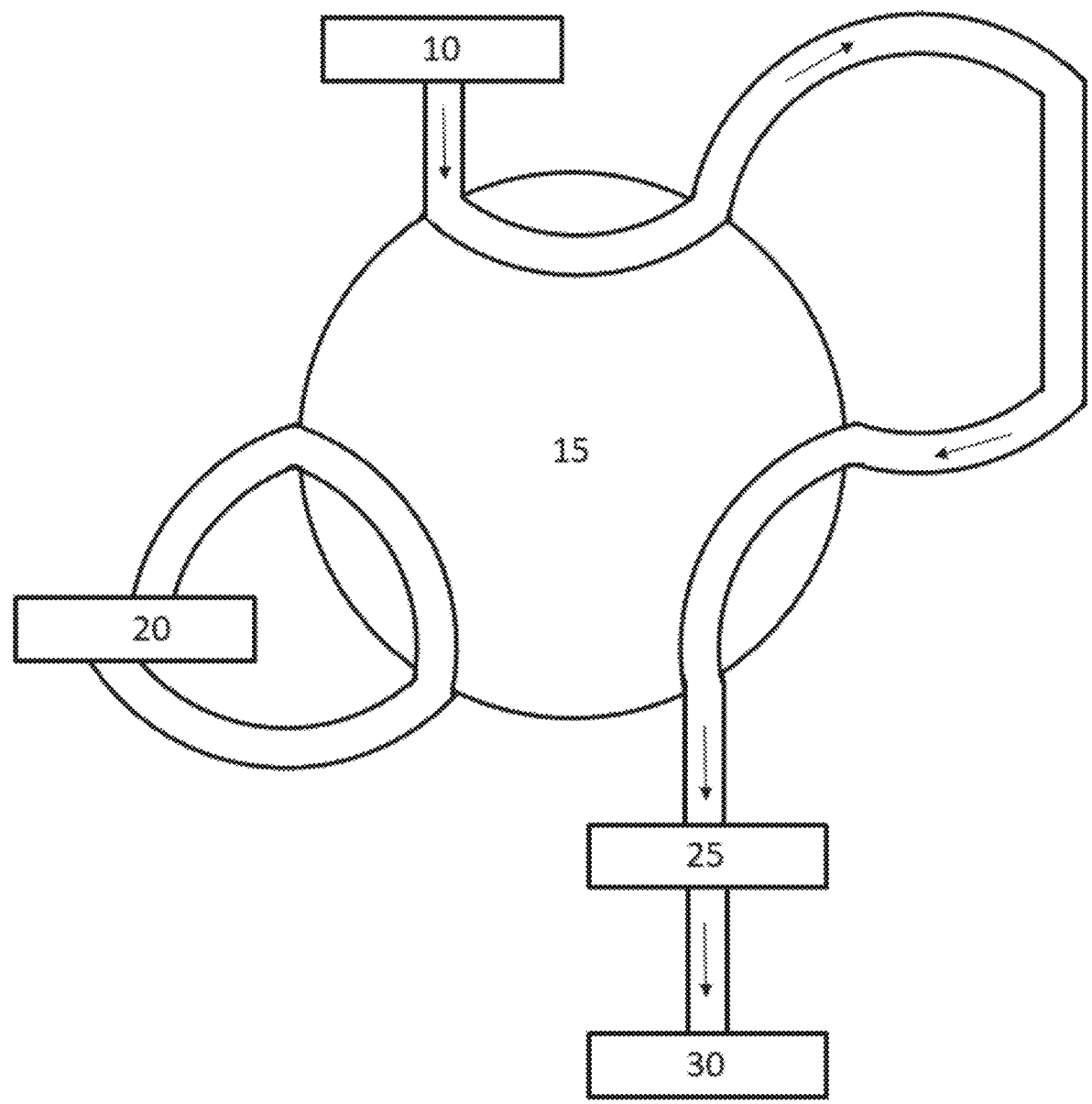
FIG. 3 schematically illustrates delivery of the derivatized analyte to the gas chromatograph.

Once any derivatized analyte has been allowed to form, the chamber is warmed to cause evaporation of any derivatized analyte. As schematically illustrated in FIG. 3, the carrier gas delivers the evaporated derivatized analyte to the gas chromatograph 30. This is shown by removal of the sample source 35 from the path, however any means of delivering carrier gas without derivatizing agent, sample, or derivatized analyte may be used, including the presence or absence of the six-port valve. Any combination of gas chromatograph and detector that is capable of detecting the derivatized analyte may be used, including a gas chromatograph-mass spectrometer. The derivatized analyte may be more amenable to detection by these means than the original analyte.

The technique is amenable to any vaporous analyte of interest that can be derivatized. The specific analyte/derivatizing agent combination may be varied. The PTV inlet temperatures and other experimental parameters may be altered to satisfy each analyte/derivatizing agent used. The technique is also amenable to any type of PTV or similar inlet, and any manner of air flow and air flow control. The valve configuration may be altered to any arrangement that allows for the collection of the derivatizing agent and the analyte vapors onto the PTV inlet. The analyte vapor may be collected prior to the derivatizing agent, or vice versa.

One example analyte that can be detected by this method is ammonia, which is not ordinarily amenable to gas chromatography. The derivatizing agent may be an alkyl chloroformate, such as butyl chloroformate. These compounds react to form butyl carbamate as the derivatized analyte as shown below. It has been shown that the use of butyl chloroformate with this method enables detection of 0.6 ppb ammonia in the sample. This may allow for detection of ammonium nitrate-based explosive devices.

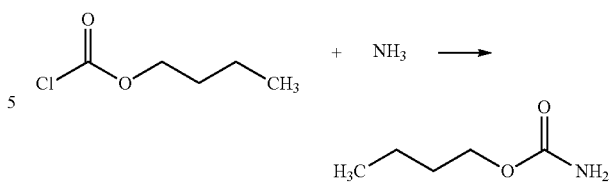

Other suitable analyte/derivatizing agent combinations include, but are not limited to, PCBs (polychlorinated biphenyls)/BSTFA (bis(trimethylsilyl)-trifluoroacetamide), aldehydes/PFBHA (pentafluorobenzyl hydroxylamine hydrochloride), primary amines/BFBAY (2,3,4,5,6-pentafluorobenzaldehyde), fatty acids/butanol, PFPDE (pentafluorophenyl diazoethane), or PDAM (pyrenyldiazomethane), and amphetamines/trifluoroacetic anhydride.

The following example is given to illustrate specific applications. The specific example is not intended to limit the scope of the disclosure in this application.

The derivatizing agent (butyl chloroformate) contained in a carboxy, was attached to one inlet of a 6-port valve. A container with solid AN, an ammonia source, was attached to another port on the valve. The valve was, in turn, attached to a cooled injection system (CIS) (Gerstel Inc.). After cryogenically cooling the CIS, the butyl chloroformate vapor was trapped on the CIS liner. The valve was then manually turned, allowing ammonia vapor to be collected onto the CIS liner now containing the derivatizing agent. Following collection of the ammonia vapor, the CIS was heated and the vapor analyzed by GC-MS.

Figure 4:
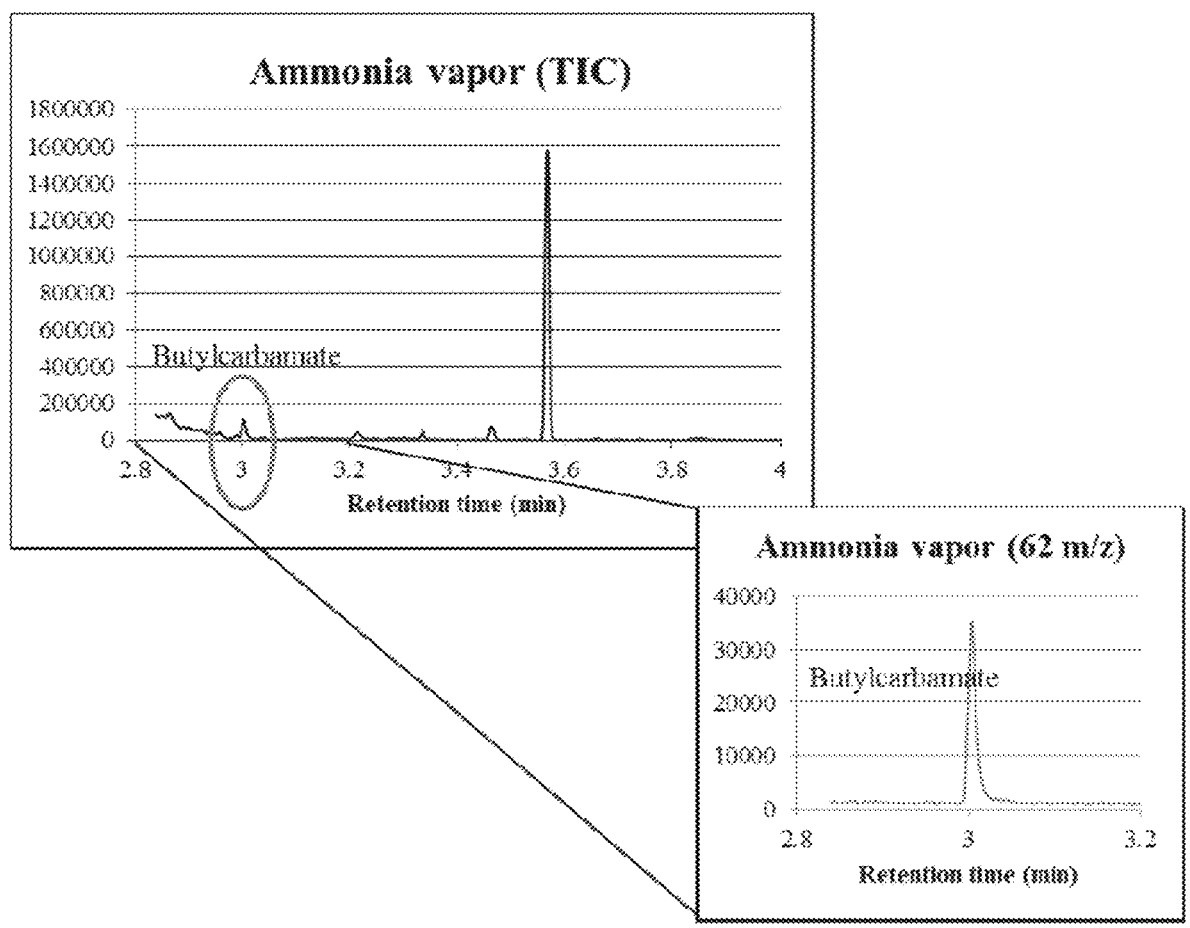
FIG. 4 shows a total ion chromatogram and extracted ion chromatogram (m/z 62) for butyl carbamate from derivatized ammonia vapor (78 ppb).

For method optimization, an ammonia permeation tube was placed in a permeation oven equilibrated to 40° C. The diluent flow rate was 207 mL/min, yielding an ammonia vapor concentration of 78 ppb at equilibrium. The following method parameters were optimized: CIS (absorption) flow rate, CIS trapping temperature, and CIS desorption flow rate. The collection volume was fixed at 1.5 L of ammonia vapor and 50 mL of butyl chloroformate vapor. FIG. 4 shows an example chromatogram using the optimized parameters. The estimated limit of detection using this method is 0.6 ppb.

Figure 5:
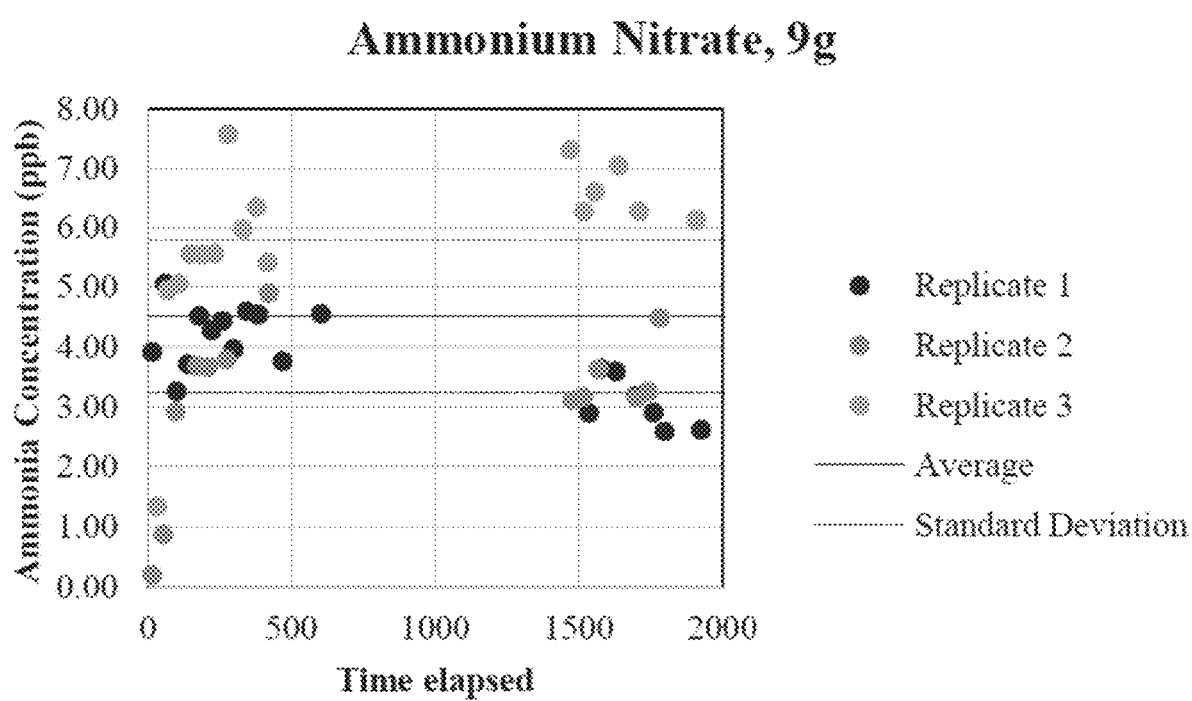
FIG. 5 shows concentration of ammonia vapor collected over time from the MODD containing three, 3 g vials of ammonium nitrate.

Following optimization, the concentration of ammonia from 9 g (3 g×three vials) of ammonium nitrate in a container was quantitated over time (approx. 33 hours), and repeated on three separate occasions (FIG. 5). The equilibrium concentration was estimated to be 4.52±1.28 ppb (by mass). While there were small deviations in equilibrium concentration over the course of a single sampling period, a larger deviation occurred between sampling periods, with a relative standard deviation (RSD) of approximately 16%. It is thus important to strictly control variables, such as ambient temperature and humidity, and the age of the ammonium nitrate material, whenever possible.

Obviously, many modifications and variations are possible in light of the above teachings. It is therefore to be understood that the claimed subject matter may be practiced otherwise than as specifically described. Any reference to claim elements in the singular, e.g., using the articles "a", "an", "the", or "said" is not construed as limiting the element to the singular.

What is claimed is:
1. A method of detecting an analyte comprising:
providing a derivatizing agent that is reactive with the analyte;
delivering the derivatizing agent into a chamber;

delivering a sample of a gas suspected of containing the analyte into the chamber before or after delivering the derivatizing agent;
  wherein the chamber is maintained at a temperature that retains the derivatizing agent and any analyte and that allows reaction between the derivatizing agent and any analyte in the chamber to form a derivatized analyte;
warming the chamber to cause evaporation of any derivatized analyte; and
delivering the evaporated derivatized analyte into a gas chromatograph column;
  wherein delivering the derivatizing agent, delivering the sample, and delivering the derivatized analyte are performed using a six-way valve.

2. The method of claim 1, wherein the chamber is a programmed temperature vaporization inlet.

3. The method of claim 1, wherein the analyte is ammonia.

4. The method of claim 1, wherein the derivatizing agent is butyl chloroformate.

5. The method of claim 1, wherein the chamber is maintained at or below 20° C. while delivering the derivatizing agent and delivering the sample.

6. The method of claim 1, wherein the chamber is warmed to at least 240° C. to evaporate the derivatized analyte.

7. The method of claim 1, further comprising:
delivering an internal standard into the chamber before, after, or between delivering the derivatizing agent and delivering the sample.

8. A method of detecting an analyte comprising:
delivering an internal standard into a chamber;
delivering a sample of a gas suspected of containing the analyte into the chamber before or after delivering the internal standard;
  wherein the chamber is maintained at a temperature that retains the internal standard and any analyte;
warming the chamber to cause evaporation of the internal standard and any analyte; and
delivering the evaporated internal standard and analyte into a gas chromatograph column;
  wherein delivering the internal standard, delivering the sample, and delivering into the gas chromatograph are performed using a six-way valve.

9. The method of claim 8, wherein the chamber is a programmed temperature vaporization inlet.

10. A method of detecting ammonium comprising:
providing a derivatizing agent that is reactive with ammonium;
delivering the derivatizing agent into a chamber;
delivering a sample of a gas suspected of containing ammonium into the chamber before or after delivering the derivatizing agent;
  wherein the chamber is maintained at a temperature that retains the derivatizing agent and any ammonium and that allows reaction between the derivatizing agent and any ammonium in the chamber to form a derivatized analyte;
warming the chamber to cause evaporation of any derivatized analyte; and
delivering the evaporated derivatized analyte into a gas chromatograph column.

11. The method of claim 10, wherein the derivatizing agent is butyl chloroformate.

12. The method of claim 10, wherein the chamber is maintained at or below 20° C. while delivering the derivatizing agent and delivering the sample.

13. The method of claim 10, wherein the chamber is warmed to at least 240° C. to evaporate the derivatized analyte.

14. The method of claim 10, further comprising:
delivering an internal standard into the chamber before, after, or between delivering the derivatizing agent and delivering the sample.

15. A method of detecting an analyte comprising:
providing butyl chloroformate;
delivering the butyl chloroformate into a chamber;
delivering a sample of a gas suspected of containing the analyte into the chamber before or after delivering the butyl chloroformate;
  wherein the chamber is maintained at a temperature that retains the butyl chloroformate and any analyte and that allows reaction between the butyl chloroformate and any analyte in the chamber to form a derivatized analyte;
warming the chamber to cause evaporation of any derivatized analyte; and
delivering the evaporated derivatized analyte into a gas chromatograph column.

16. The method of claim 15, wherein the chamber is a programmed temperature vaporization inlet.

17. The method of claim 15, wherein the chamber is maintained at or below −20° C. while delivering the derivatizing agent and delivering the sample.

18. The method of claim 15, wherein the chamber is warmed to at least 240° C. to evaporate the derivatized analyte.

19. The method of claim 15, further comprising:
delivering an internal standard into the chamber before, after, or between delivering the derivatizing agent and delivering the sample.

* * * * *

UNITED STATES PATENT AND TRADEMARK OFFICE
CERTIFICATE OF CORRECTION

PATENT NO.       : 10,648,955 B2
APPLICATION NO.  : 15/903166
DATED            : May 12, 2020
INVENTOR(S)      : Lauren E. DeGreeff and Christopher J. Katilie It is certified that error appears in the above-identified patent and that said Letters Patent is hereby corrected as shown below:

In the Claims

Claim 5, Column 5, Lines 23-25:
5. The method of claim 1, wherein the chamber is maintained at or below 20°C while delivering the derivatizing agent and delivering the sample.

Should be:
5. The method of claim 1, wherein the chamber is maintained at or below –20°C while delivering the derivatizing agent and delivering the sample.

Claim 10, Column 5, Line 48-Column 6, Line 12:
10. A method of detecting ammonium comprising:
providing a derivatizing agent that is reactive with ammonium;
delivering the derivatizing agent into a chamber;
delivering a sample of a gas suspected of containing ammonium into the chamber before or after
    delivering the derivatizing agent;
        wherein the chamber is maintained at a temperature that retains the derivatizing agent and any
            ammonium and that allows reaction between the derivatizing agent and any
            ammonium in the chamber to form a derivatized analyte;
warming the chamber to cause evaporation of any derivatized analyte; and
delivering the evaporated derivatized analyte into a gas chromatograph column.

Should be:
10. A method of detecting ammonia comprising:
providing a derivatizing agent that is reactive with ammonia;
delivering the derivatizing agent into a chamber;
delivering a sample of a gas suspected of containing ammonia into the chamber before or after
    delivering the derivatizing agent;
        wherein the chamber is maintained at a temperature that retains the derivatizing agent and any Signed and Sealed this
Fourteenth Day of July, 2020

Andrei Iancu
*Director of the United States Patent and Trademark Office* ammonia and that allows reaction between the derivatizing agent and any ammonia in the chamber to form a derivatized analyte;
warming the chamber to cause evaporation of any derivatized analyte; and
delivering the evaporated derivatized analyte into a gas chromatograph column.

Claim 12, Column 6, Lines 14-16:
12. The method of claim 1, wherein the chamber is maintained at or below 20°C while delivering the derivatizing agent and delivering the sample.

Should be:
12. The method of claim 1, wherein the chamber is maintained at or below –20°C while delivering the derivatizing agent and delivering the sample.